(12) United States Patent
Hoying

(10) Patent No.: US 11,492,579 B2
(45) Date of Patent: Nov. 8, 2022

(54) VASCULARIZED IN VITRO ARRAYS OF LIVING CELLS

(71) Applicant: Advanced Solutions Life Sciences, LLC, Louisville, KY (US)

(72) Inventor: James Beatty Hoying, Louisville, KY (US)

(73) Assignee: Advanced Solutions Life Sciences, LLC, Louisville, KY (US)

( * ) Notice: Subject to any disclaimer, the term of this patent is extended or adjusted under 35 U.S.C. 154(b) by 1078 days.

(21) Appl. No.: 16/076,051

(22) PCT Filed: Apr. 13, 2018

(86) PCT No.: PCT/US2018/027516
§ 371 (c)(1),
(2) Date: Aug. 7, 2018

(87) PCT Pub. No.: WO2018/191636
PCT Pub. Date: Oct. 18, 2018

(65) Prior Publication Data
US 2021/0214662 A1    Jul. 15, 2021

Related U.S. Application Data

(60) Provisional application No. 62/485,447, filed on Apr. 14, 2017.

(51) Int. Cl.
*C12M 3/00* (2006.01)
*C12M 1/12* (2006.01)
(Continued)

(52) U.S. Cl.
CPC ............ *C12M 21/08* (2013.01); *C12M 23/06* (2013.01); *C12M 23/12* (2013.01); *C12M 23/16* (2013.01); *C12M 25/14* (2013.01)

(58) Field of Classification Search
CPC ...... C12M 23/06; C12M 21/08; C12M 23/16; C12M 23/12; C12M 25/14; C12M 33/00; C12M 25/00
See application file for complete search history.

(56) References Cited

U.S. PATENT DOCUMENTS

| | | | |
|---|---|---|---|
| 6,548,263 B1 * | 4/2003 | Kapur | C12M 25/06 216/2 |
| 2008/0014589 A1 * | 1/2008 | Link | G01N 21/05 137/896 |

(Continued)

FOREIGN PATENT DOCUMENTS

| | | |
|---|---|---|
| JP | 2005168494 A | 6/2005 |
| WO | 20090148507 A1 | 12/2009 |

OTHER PUBLICATIONS

Cahill et al. Vascular endothelium e Gatekeeper of vessel health. Atherosclerosis (epub. Mar. 9, 2016), 248, 97-109. (Year: 2016).*

(Continued)

*Primary Examiner* — Sean C. Barron
(74) *Attorney, Agent, or Firm* — Dinsmore and Shohl

(57) ABSTRACT

High-throughput column arrays of vascularized living parenchyma/tissue having pillars dispersed in specialized configurations and arrangements substantially vertically through the column to provide support, passive or active perfusion, and access to internal portions of tissue for analytical sampling needs, along with 3-D printing methods of manufacture and analytical screening methods employing the column arrays.

20 Claims, 15 Drawing Sheets

(51) Int. Cl.
  *C12M 1/32* (2006.01)
  *C12M 3/06* (2006.01)

(56) References Cited

U.S. PATENT DOCUMENTS

| | | |
|---|---|---|
| 2009/0017439 A1 | 1/2009 | Shimko et al. |
| 2010/0112690 A1 | 5/2010 | Eddington |
| 2010/0216241 A1 | 8/2010 | Yu et al. |
| 2012/0225101 A1 | 9/2012 | Kao et al. |
| 2014/0220555 A1 | 8/2014 | Chen et al. |
| 2014/0348706 A1* | 11/2014 | Rahman .............. G01N 33/4836 422/502 |
| 2015/0174573 A1* | 6/2015 | Esch .................... G03F 7/2022 430/320 |
| 2016/0054303 A1 | 2/2016 | Hanson |
| 2017/0000919 A1 | 1/2017 | Childers et al. |
| 2017/0009194 A1 | 1/2017 | Golway et al. |

OTHER PUBLICATIONS

Extended European Search Report (EESR) for corresponding EP Application No. 187784111.9 dated Mar. 12, 2021.
English Machine Translation of JP2005168494A.
International Search Report and Written Opinion for corresponding PCT No. PCT/US2018/27516 dated Aug. 23, 2018.
Canadian Office Action in reference to Application No. 3,059,983 filed Apr. 13, 2018.
Miller et al., "Rapid casting of patterned vascular networks for perfusable engineered 3D tissues", Nature Materials, 11(9), pp. 768-774, Sep. 2012 (Sep. 2012).
Korean First Office Action dated Jul. 15, 2022 pertaining to KR application No. 10-2019-7032686 filed Nov. 4, 2019, pp. 1-11.
Müller, M. et al. "Printing Thermoresponsive Reverse Molds for the Creation of Patterned Two-component Hydrogels for 3D Cell Culture" Journal of Visualized Experiments, Jul. 10, 2013, pp. 1-9, Issue 77.

* cited by examiner

| | 1 | 2 | 3 | 4 | 5 | 6 | 7 | 8 | 9 | 10 | 11 | 12 |
|---|---|---|---|---|---|---|---|---|---|---|---|---|
| A | | 20x10$^6$ Hepatocytes-Untreated | | 15x10$^6$ Hepatocytes-Untreated | | 10x10$^6$ Hepatocytes-Untreated | | 2x10$^6$ Hepatocytes (pellet)-Untreated | | 1x10$^6$ NPC-Untreated | | |
| B | | 20x10$^6$ Hepatocytes-Dextromethorphan Level 5 | | 15x10$^6$ Hepatocytes-Dextromethorphan Level 5 | | 10x10$^6$ Hepatocytes-Dextromethorphan Level 5 | | | | 1x10$^6$ NPC-Dextromethorphan Level 5 | | |
| C | | 20x10$^6$ Hepatocytes-Dextromethorphan Level 5 | | 15x10$^6$ Hepatocytes-Acetaminophen Level 5 | | 10x10$^6$ Hepatocytes-Acetaminophen Level 5 | | | | 1x10$^6$ NPC-Acetaminophen Level 5 | | |
| D | | 20x10$^6$ Hepatocytes-Acetaminophen Level 5 | | 15x10$^6$ Hepatocytes-Acetaminophen Level 1 | | 10x10$^6$ Hepatocytes-Acetaminophen Level 1 | | | | 1x10$^6$ NPC-Acetaminophen Level 1 | | |
| E | | 20x10$^6$ Hepatocytes-Acetaminophen Level 3 | | | | | | | | | | |
| F | | 20x10$^6$ Hepatocytes-Acetaminophen Level 1 | | | | | | | | | | |
| G | | | | | | | | | | | | |
| H | | | | | | | | | | | | |

FIG. 3

VASCULARIZED IN VITRO ARRAYS OF LIVING CELLS

PRIORITY CLAIM

This application claims benefit under 35 U.S.C. § 119(e) to U.S. provisional application No. 62/485,447, filed Apr. 14, 2017, the entire disclosure of which is incorporated herein by reference.

TECHNICAL FIELD

The technical field relates to 3D-printed in vitro microfluidic vascularized arrays of living cells that are passively or actively perfusable, and to a high through-put biomedical investigational platform utilizing the arrays, with specific applications in the fields of pharmaceutical screening/testing, tissue and organ fabrication and transplant, toxicity screening, and for investigating response of vasculature to a variety of stimuli and conditions.

BACKGROUND

Vascularized tissue engineering is a relatively new, rapidly evolving technology with the potential to completely shift the paradigm with respect to meeting the needs for organ transplantation and providing regenerative therapeutic technologies. However, additional investigation into basic vascular biology is required before the full promise of this technology can be realized. Providing a scalable platform that enables rapid high throughput investigation of living cells, in particular parenchymal cells and tissues, via diffusive and/or active perfusion of nutrients, putative therapeutics, and other investigatory agents is paramount.

Significant limitations in the fabrication of 3D tissue constructs for a variety of applications is the ability to impart internal structure and organization to the construct, and the ability to provide necessary nutrients or investigative agents to structures more than a few cells thick. Such organization is necessary to mimic native tissue and to enable relevant and useful tissue responses and function not achieved by current artificial tissue designs, which involve mixing of different tissue construction elements (e.g. cells, matrix, etc.) into homogeneous constructs such as spheroids, cell aggregates, embryoid bodies, or well-plated cell constructs. In addition, these currently practiced bulk-phase designs are restricted in size due to the diffusion limitations, resulting in cell/tissue death and dysfunction. Generally, maintaining living tissue via diffusive transport alone limits the thickness of the tissue to less than about 100-200 microns. Producing a perfusable microvascular network within a tissue construct is therefore considered critical to fabrication of larger constructs. Finally, current practices limit access to the interior of the tissue construct for desired analytical sampling often needed in many applications.

Thus, there remains a compelling need in the art of artificial tissue fabrication and analytics to address the limitations of absence of internal structure, restricted construct size, and sampling access.

SUMMARY

Accordingly, embodiments of the invention address and overcome these and other deficiencies by providing a scalable platform by which simultaneously, 1) cells and cell compartments within a tissue construct may be organized, 2) routes of diffusion and/or perfusion may be established within the tissue construct, and 3) access ports to the tissue construct interior are available. Greater flexibility is provided in tissue structural design, implementation of passive or active perfusion, and ease of sampling for a variety of analytics. Furthermore, embodiments of the invention are particularly suited to high-throughput formats. Embodiments of the invention are modular in design, enabling more complex tissue construct fabrication while preserving the beneficial utilities of the module.

One embodiment provides a column array comprising a set of columnar spaces, each columnar space having a base and comprising a pillar volume and a cellular volume, said pillar volume being divided into one or more pillars in an arrangement, the one or more pillars each extending from the base within the columnar space, each pillar being surrounded by cellular volume, said cellular volume comprising viable cells, wherein "viable" is defined as comprising greater than 50% living cells after one week. In some embodiments the pillar volume comprises a hydrogel matrix, and in other embodiments the pillar volume is a pillar space having been formed from a sacrificial material that is washed out of the pillar subsequent to printing.

Another embodiment is directed to a multiple well-plate platform comprising an embodiment of a column array according to aspects of the invention. The multiple well-plate platform may comprise, for example, 384, 96, 49, 24, 12, or 6 wells and may be precisely fabricated via 3-D printing.

Another embodiment provides a method of making a column array comprising a set of columnar spaces, each columnar space having a base and comprising a pillar volume and a cellular volume, said pillar volume being divided into one or more pillars in an arrangement, the one or more pillars each extending from the base within the columnar space, each pillar being surrounded by cellular volume. Generally, the method comprises 3-D printing the pillar volume with a matrix material, and 3-D printing the cellular volume with a bio-ink or casting the cellular volume around the pillar volume. In embodiments that require pillar spaces the pillar volume is printed with a sacrificial material that is washed out subsequent to printing or casting the cellular volume.

Other embodiments are directed to methods for screening putative agents for specific cellular toxicity. According to some embodiments, the methods comprise providing a multiwell plate comprising a column array of pillar spaces within a cellular volume, contacting the cellular volume with the putative agent via the pillar spaces, and measuring changes in viability of cells in the cellular volume versus a control. Methods of screening putative agents for effect on angiogenesis are also provided. Embodiments provide a multiwell plate according comprising a column array of pillar spaces within a cellular volume, wherein the cellular volume comprises a microvasculature derived from adding substantially intact native microvessels to the cellular volume and subjecting the microvessels to maturing conditions; contacting the cellular volume with the putative agent via adding a composition of a putative agent to the pillar volume, and measuring changes in the microvasculature versus a control.

These and other embodiments and aspects will be more fully detailed and clarified by reference to the Figures and Detailed Description below. Figures are provided to illustrate principles and specific embodiments of the invention

BRIEF DESCRIPTION OF THE FIGURES

FIG. 1A: digital model of the pillars; FIG. 1B: top view of the actual pillars fabricated with a sacrificial hydrogel; FIG. 1C: top view highlighting the structural organization and short diffusion distances of the final tissue construct after removal of the pillars. FIG. 1D: high magnification of the pillar volume/tissue interface.

FIG. 2A: cell morphology and FIG. 2B viability results for four-day cultures of combined primary hepatocytes with non-parenchymal cells (NPCs). FIG. 2C and FIG. 2D show live/dead fluorescent staining; Open arrows=negative cells, closed arrows=positive (i.e. dead) cells.

FIG. 3: Sets forth the layout of drug treatments for Example 2.

FIG. 6A: digital model of the pillars; FIG. 6B: top view of the actual pillars fabricated with a sacrificial hydrogel—changing the diameter of the pillars changes the between-pillar spacing, which in turn enables the spontaneous reorganization of the cells within the construct; FIG. 6C: top view of a 96 well-plate containing the structured constructs treated with different doses of drugs showing differential dose responses (open arrows)—inset is a single construct, removed from a well; FIG. 6D: high magnification of the pillar volume/tissue interface showing that a tissue has formed, even without the addition of a scaffold in the initial fabrication.

FIG. 7A: top view of the actual pillars fabricated with a sacrificial hydrogel; FIG. 7B: top view of the constructed tissue after removal of the pillars.

FIG. 8A: top view of one of the pillar spaces and adjacent tissue compartment containing microvessels; FIG. 8B: high magnification of the highlighted area in FIG. 8A showing active angiogenesis supported by the structured construct.

DETAILED DESCRIPTION

Figure 1A:
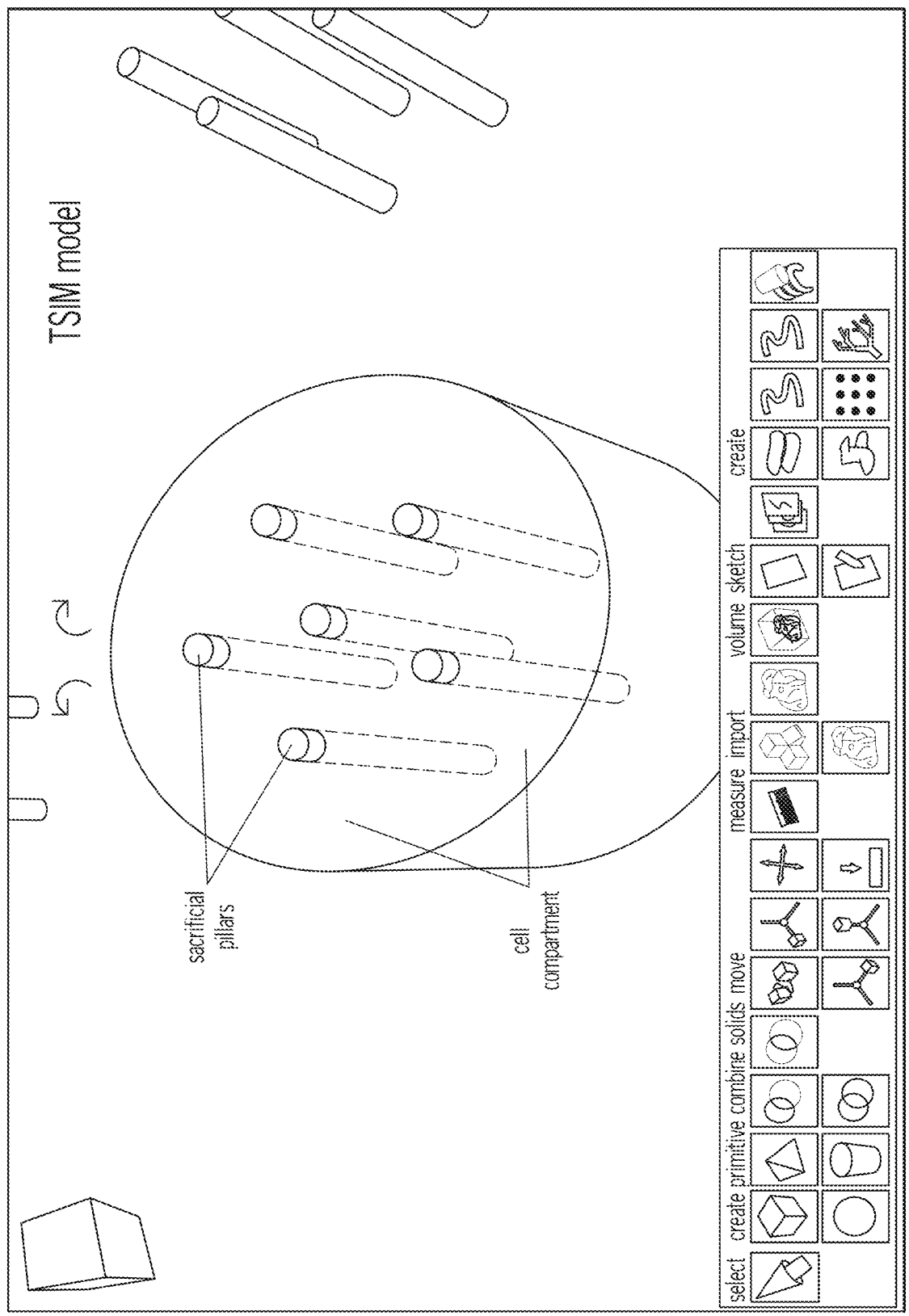
FIGS. 1A-1D: Illustrate an exemplary embodiment in which five sacrificial pillars, 1 mm in diameter, are fabricated prior to the incorporation of a cell/collagen mixture around the pillars. Pillars are then sacrificed, leaving behind pillar volumes within the tissue construct, around which the cells of the construct continue to grow and function.

Embodiments of the invention relate to 3-D printing of column arrays for fabrication of viable tissue constructs and for high-through put investigation of viable cells and tissues. Multiple pillars may be printed in a variety of arrangements and shapes within the wells of a multi-well plate. Cellular parenchyma, with or without microvessels and with or without matrix, are then cast around these pillars within the well to form a tissue construct. The pillars may be printed from supporting matrix, or from sacrificial material which may be removed (i.e. washed-out), leaving behind pillar spaces dispersed throughout the cellular parenchyma/tissue construct. The tissue construct may be perfused via a perfusion system connected to the pillar volume or may be perfused via passive diffusion.

One embodiment is directed to column arrays comprising a set of columnar spaces, each columnar space having a base and comprising a pillar volume and a cellular volume, said pillar volume being divided into one or more pillars in an arrangement, the one or more pillars each extending from the base within the columnar space, each pillar being surrounded by cellular volume, said cellular volume comprising viable cells, wherein "viable" is defined as comprising greater than 50% viable cells after one week. A pillar volume may comprise a material such as a hydrogel, liquid, or solid, or may be a space substantially devoid of material and may be referred to herein as a pillar space. Where the volume comprises a material, it may provide support to the cellular volume. A pillar volume provides access to the interior of the cellular volume.

Viability assays are well-known in the art. Generally a viability assay determines the ability of cells or tissues to maintain or recover viability, which is provided as a quantifiable percentage between 0% and 100%. An on-line manual reviewing commonly available and utilized cell viability assays is Riss, Terry L. et al. "Cell Viability Assays" published May 1, 2013, last updated on Jul. 1, 2016, the entire contents available as of Jul. 1, 2016 being incorporated herein by reference. Viability assays may be based on mechanical activity, motility, contraction, mitotic activity, cellular uptake or metabolic conversion and the like. An assay that purports to establish percent "living" of a total number of cells is considered a viability assay for purposes of defining the scope of the invention.

According to specific embodiments, the one or more pillars extend substantially vertically from the base. "Substantially" herein means within 10% of perpendicular from the base. Other orientations are contemplated depending on analytical or clinical need. According to some embodiments, the cellular volume comprises a supporting hydrogel matrix "scaffold" comprising the viable cells and, in other specific embodiments, microvasculature. Scaffold-free embodiments are also contemplated wherein the cellular volume comprises cells and other native cellular material and/or microvessels, but does not comprise a matrix material.

According to specific embodiments, the cellular volume comprises viable cells selected from one or more of normal cells, diseased cells, stem cells, endothelial cells, stromal cells, myocardial cells, hepatocytes, renal cells, tumor cells, liver cells, pancreatic cells, muscle cells, brain cells, kidney cells, and patient-specific cells. According to more specific embodiments, the cellular volume comprises parenchymal cells and forms a tissue.

The hydrogel matrix may be selected from a natural hydrogel, a synthetic hydrogel, and hybrid natural and synthetic hydrogels. Non-limiting examples of suitable natural hydrogels include one or more of a collagen, gelatin, fibrin, and a polysaccharide selected from hyaluronic acid (HA), agarose, alginate, and chitosan. Non-limiting examples of suitable synthetic hydrogels include one or more of polydimethylsiloxane (PDMS), polyethylene glycol (PEG), poly(lactic-co-glycolic acid) (PLGA) and polyglycerol sebacate (PGS) polymers. Combinations of natural and synthetic hydrogels are also contemplated.

According to some embodiments, the cellular volume further comprises a microvasculature. According to specific embodiments, the microvasculature is formed from adding substantially intact native microvessels to the cellular volume and subjecting the native microvessels to maturing conditions. The present investigators recently disclosed the formation of an adaptable microvasculature in a gel matrix formed from incorporating intact native microvessels into the gel, and subjecting the microvessels to maturing conditions. This is described in detail in U.S. patent application Ser. No. 15/202,675 (the Hoying application), the entire disclosure of which is incorporated herein by this reference. According to very specific embodiments, the intact native microvessels derive from adipose tissue.

A sacrificial casting strategy may be employed whereby pillars comprising a thermos-reversible hydrogel or glassing material are 3-D printed on the base. The cellular volume comprising viable cells such as cellular parenchyma, with or without microvessels is then printed or cast around the pillars. The sacrificial hydrogel is washed/flushed out leaving pillar spaces traversing in desired orientations throughout the cellular volume, which forms the tissue construct. According to very specific embodiments, the pillar spaces extend substantially vertically through the tissue construct from the base. The pillars forming the pillar volume and pillar space may be printed in a variety of shapes including but not limited to pillars having a circular, triangular, rectangular, pentagonal or hexagonal cross section. A person of ordinary skill in the art will readily envision the variety of potential shapes providing a different number of interactive or sampling facades between the pillar space and the cellular volume/tissue construct. According to some embodiments, the pillar volume or pillar space may be connected via at least one inlet port to a perfusion system whereby maturation of the immature microvessels is driven by controlled pressure or flow. According to other specific embodiments, perfusion of the cellular volume is achieved by passive diffusion between the pillar volume and the cellular volume, and in other specific embodiments perfusion is achieved actively by connecting a pillar volume to a perfusion system, for example a pumping mechanism. Non-limiting examples of pumping mechanisms for achieving perfusion include a pressure-driven flow controller, a peristaltic pump, and a syringe mechanism, which may or may not be powered by a motor. Static columnar arrays are also contemplated. In very specific embodiments, subjecting the microvessels to maturing conditions comprises defining perfusion hemodynamics to provide a shear stress sufficient to induce endothelial sprouting, for example the provided shear stress may be greater than or equal to 10 dynes/cm$^2$.

The devices described in the Hoying application were characterized therein as vascularized in vitro perfusion devices and comprised a 3D matrix with or without parenchyma/cells connected to a network of microfluidic channels formed via a sacrificial strategy. According to embodiments of the currently disclosed invention, the microfluidic channel network is replaced by a set of pillar spaces through which the microvasculature in the cellular compositions may be perfused. According to a specific "scaffold-free" embodiment, there is substantially no matrix in the cellular volume and microvessels may be embedded in a tissue comprised almost entirely of parenchyma.

The pillar spaces may serve multiple purposes, for example:
1. Providing increased surface area for cell/tissue:media exchange. This is not only relevant to supporting tissue construct viability, but also improved delivery of drugs, tracers, soluble factors, etc;
2. Providing perfusion access where desired. Using a microfluidic manifold, the pillar spaces can be connected to perfusion systems, thereby pressurizing the spaces and, depending on additional channel connections and/or a microvasculature, perfuse the tissue construct;
3. Providing structural organization to the tissue enabling native cell behavior and function (this is particularly the case where pillar volumes are formed without a sacrificial material; and
4. Providing sampling access ports within the tissue compatible with analytics.

Various arrangements of pillars may be printed on the columnar base, depending on analytical or clinical need. Specific embodiments contemplate that at least two pillars are in fluid communication via at least one cross-connecting channel. The cross-connecting channel may be printed at any orientation between the pillars, for example in a very specific embodiment the cross-channel is horizontal and located/connected at any level along the height of the pillars. In other very specific embodiments the cross-channel fluidly connects a top portion of one pillar to a bottom portion of a second or more pillars. In one very specific embodiment the arrangement comprises a hub-and-spoke arrangement wherein one pillar is located at a center/axial position relative to two or more surrounding pillars, and at least one, some or all surrounding pillars are connected by at least one connecting channel to the center/axial pillar. In specific embodiments the one or more surrounding pillars are located between the axial/center position and an edge of the column. Surrounding pillars may be located at any position along the radius of the column, and embodiments are contemplated wherein surrounding pillars are located at different positions along the radius in the same arrangement. Embodiments are contemplated wherein different pillars on the same well/base have different diameters or different shapes.

Multiple configurations of column arrays are contemplated. Non-limiting examples include:
1. Cellular volume−matrix; +pillars; (scaffold free)
2. Cellular volume+matrix; +pillars
3. Cellular volume+/−matrix; +pillars; with perfusion;
4. Cellular volume+/−matrix+microvessels; +pillars; without perfusion (static)
5. Cellular volume+/−matrix+microvessels; +pillars; with perfusion
6. 1-5 except the cellular volume does not comprise parenchymal cells.

According to specific embodiments, the pillar density and array arrangement in the columnar space may be varied. As used herein, parenchyma cells comprise any primary, cultured, or derived parenchymal cells. Other cells that may be included in the cellular volume with or without parenchymal cells include non-parenchyma cells, stroma cells, accessory cells, etc. According to very specific embodiments, the cellular volume comprises primary hepatocytes+primary non-parenchyma live cells+/−1 primary adipose microvessels.

Embodiments of the invention are particularly suitable for high-through put analytics. 3-D printing enables extreme levels of dimensional precision and cellular/sub-cellular resolution. According to specific embodiments, a column array is printed in a plurality of wells on a multiple well-plate platform. The printed arrays may be the same or different in configuration and arrangement in each well. The multiple well-plate platform may comprise one of the standard 384, 96, 49, 24, 12, 6-well plates, or any desired number of wells.

One embodiment is directed to methods for making a column array comprising a set of columnar spaces, each columnar space having a base and comprising a pillar volume and a cellular volume, said pillar volume being divided into one or more pillars in an arrangement, the one or more pillars each extending from the base within the columnar space, each pillar being surrounded by cellular volume. The methods comprise 3-D printing the pillars/pillar volume with a matrix material, and 3-D printing the cellular volume with a bio-ink or casting the cellular volume around the pillar volume. As noted above, pillar spaces may be formed by printing the pillar volume with a matrix material comprising a sacrificial material and removing the sacrificial material subsequent to printing or casting the cellular volume. According to specific embodiments, the sacrificial material is selected from glass and polymer. In very specific embodiments, the polymer comprises a pluronic thermosensitive hydrogel, and in even more specific embodiments, the pluronic hydrogel comprises an F127 hydrogel.

Methods of screening putative agents for specific cellular toxicity are provided. The methods comprise providing a multiwell plate and fabricating an embodiment of the column array in a plurality of the wells. The cellular volume is contacted with one or more putative agents via the pillar volume, and changes in viability of the cells in the cellular volume are measured and compared to a control. Suitable controls, both positive and negative, are readily designed and identifiable to a person of skill in the art. For example, the control may be an agent known as toxic or an agent known as neutral to provide a baseline for measuring relative effect on the cell viability. In a specific embodiment, a composition comprising a putative agent is added to a pillar volume of a set of wells in the plate, and control is added to a second set of wells, and changes in viability of cells in the experimental cellular volume versus the control cellular volume are measured. The inventive array permits sampling of the cellular volume via a pillar space at any vertical depth of the cellular volume and through a substantial horizontal plane, depending on the pillar arrangement, providing a singularly unique ability to control for or avoid the effects of positional gradients and/or positional differences in effects/results.

Methods of screening putative agents for effect on angiogenesis are also provided. Column arrays according to the invention are constructed in a plurality of wells of a multiwell plate. The cellular volume comprises viable cells and further comprises a microvasculature derived from adding substantially intact native microvessels to the cellular volume and subjecting the microvessels to maturing conditions. The microvasculature is contacted with putative agents via adding a composition of a putative agent to the pillar volume. Changes in the microvasculature are assessed versus a control. In specific screening embodiments, the pillar volume is connected to a perfusion system and the composition comprising a putative agent perfuses the cellular volume. The perfusion system may comprise a perfusion chamber.

EXAMPLES

The following examples are set forth to illustrate specific aspects and embodiments of the invention and should not be construed as limiting the scope thereof.

Example 1

A BioAssemblyBot® robotic assembly workstation and Tissue Structure Information Modeling (TSIM®) software available from Advanced Solutions Life Sciences, LLC (ASLS) were utilized to 3-D print hepatocellular tissue structures for biomarker screening. Details of the robotic assembly workstation utilized are set forth in U.S. Pat. No. 9,910,935, the entire disclosure of which is incorporated herein by reference. The testing included generating 3-D printed liver cell cultures that remained viable for at least 14 days.

Static Assay: provide two 3D printed structure types and cell type configurations assessing viable liver tissue 3D printed assays.

Cells: Liver Cells with their respective media and chemical compounds were provided by Nucro-Technics and shipped to ASLS's lab in Louisville, Ky.

Figure 1B:
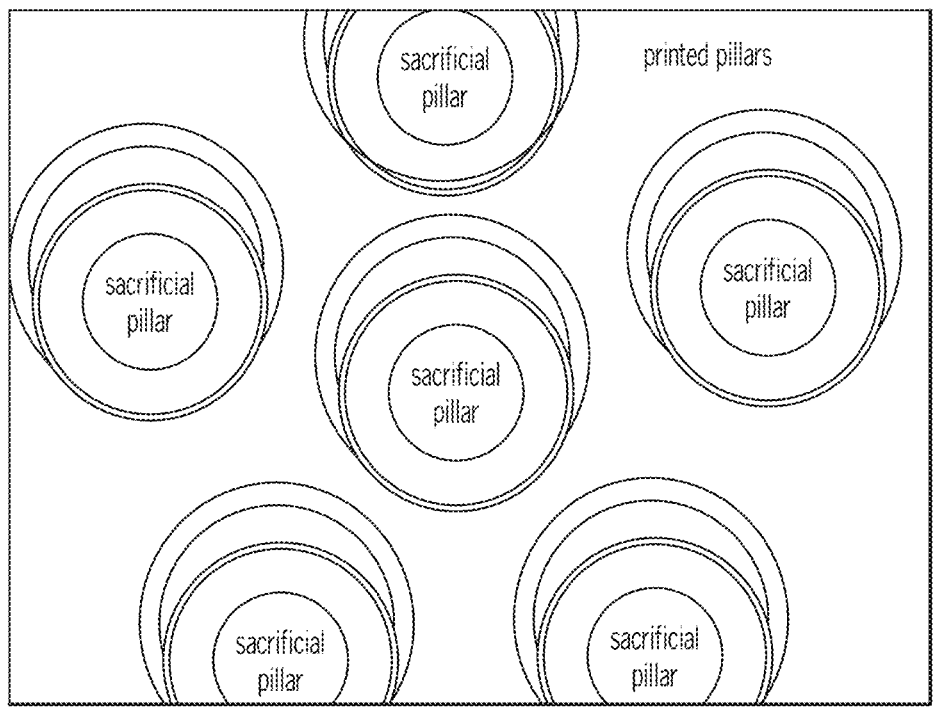

Cell Printing: Two 3-D cell culture designs were developed and generated. The lay-out design of the pillars was based on achieving "honey-comb"-like structures within each well of a 96-well plate using a sacrificial material approach to create either 3 or 6 cavities in collagen gels for each well (FIGS. 1A and 1B). For each, primary Hepatocytes (Heps) (250,000/well) mixed with primary NPCs (125,000/well) were embedded in collagen (3 mg/ml) and deposited around the pillars. The sacrificial pillars were then dissolved and washed away leaving cavities for media exchange. The design enables 1) compartmentalizing different cell types, and 2) creating better media exchange with cell compartments.

An initial proposed design was explored involving isolated pillars, but the exemplary honeycomb design improved cell capacity and design flexibility. Mixed cell (Heps+NPCs in one compartment) cultures were established with rat cells in 96 well plates. Phase images were taken over the $1^{st}$ week. At day 4, one column of wells (8 total) were assessed via a live/dead fluorescence assay (live cells fluoresce green while dead/dying cells fluoresce red) and again at day 7. Notably, the live cytoplasmic stain, calcein green, was not effective in the collagen gels (which strongly autofluoresces in the green and therefor green nuclear dye was used in the next round to improve signal to noise.

Figure 1C:
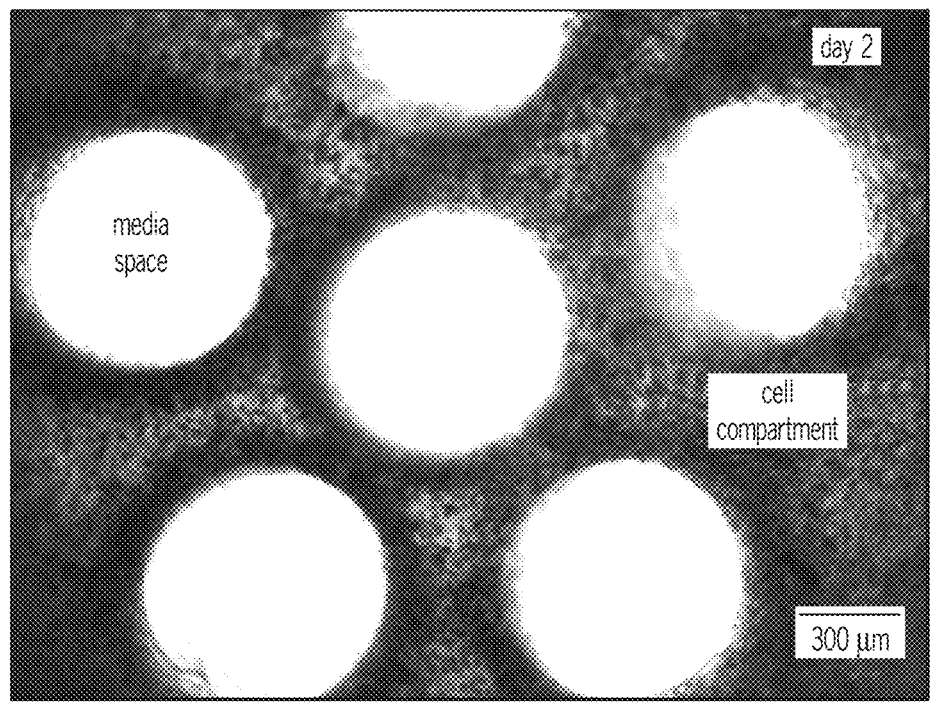
Figure 1D:
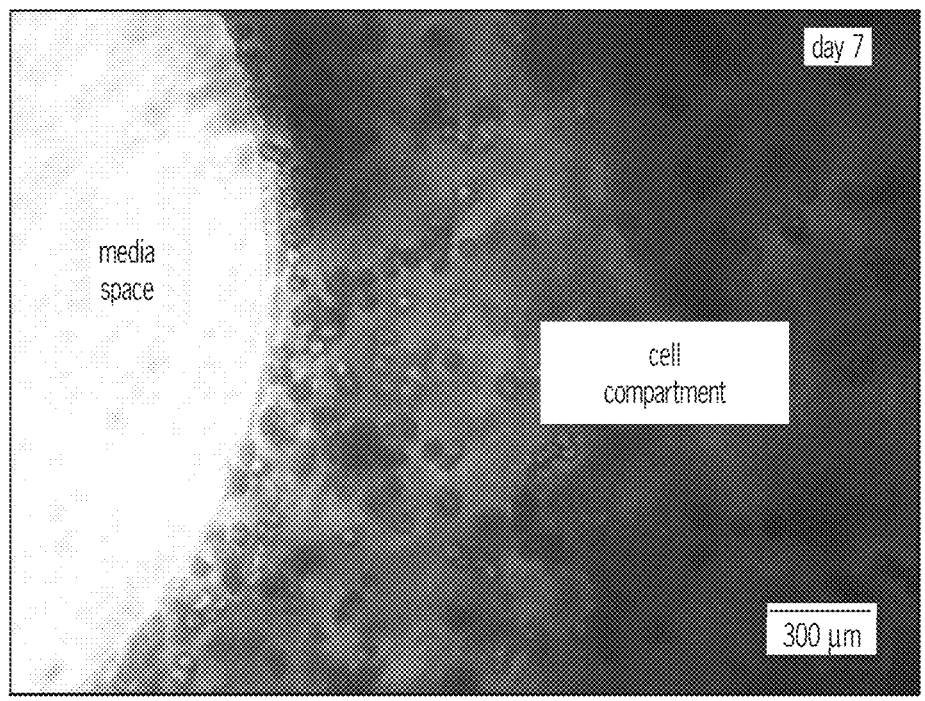
Figure 2A:
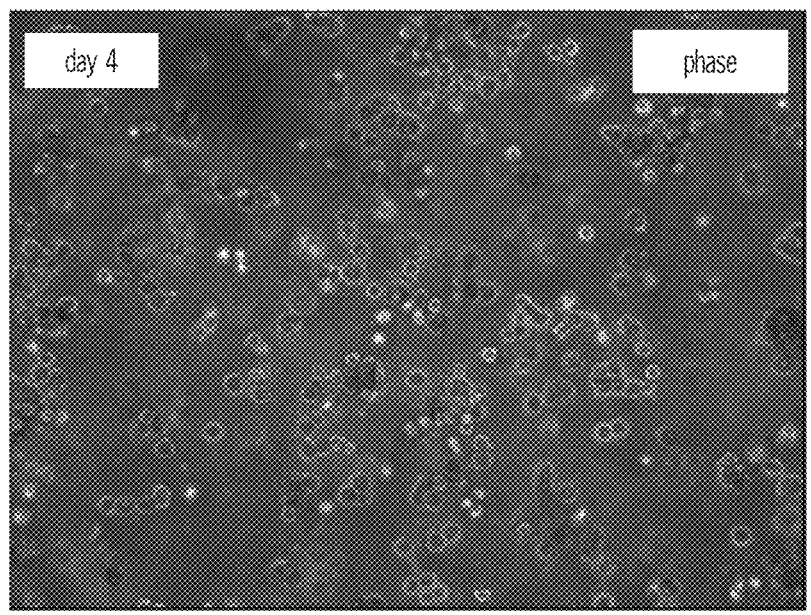
FIGS. 2A-2D: Sets forth results from Example 2 showing
Figure 2B:
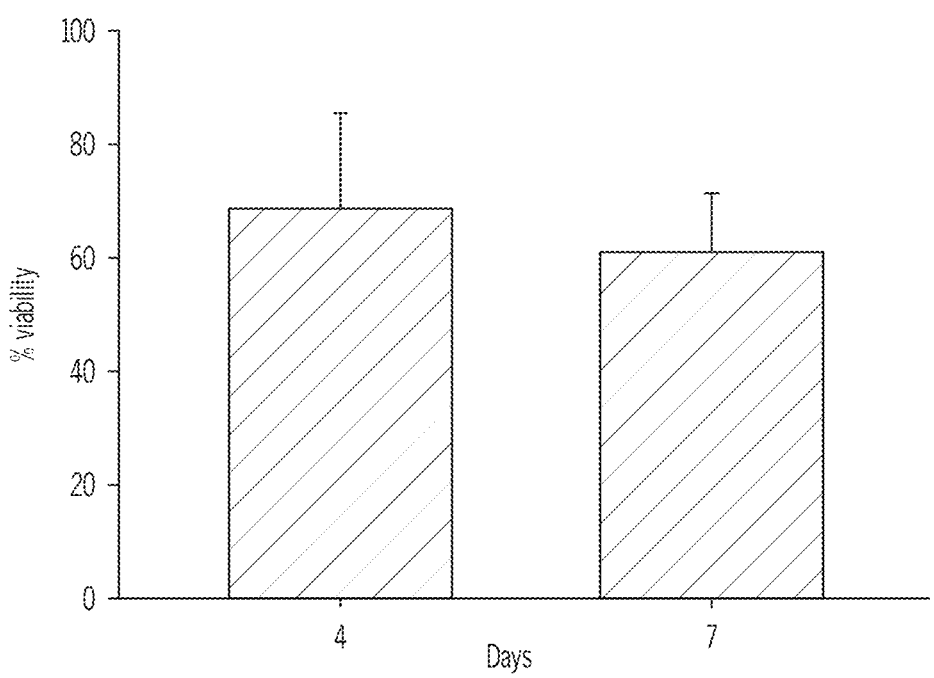
Figure 2C:
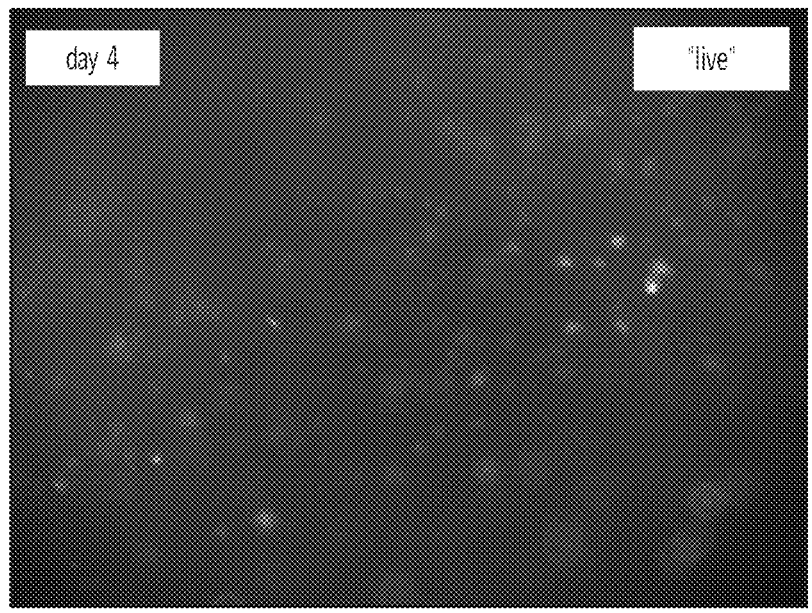
Figure 2D:
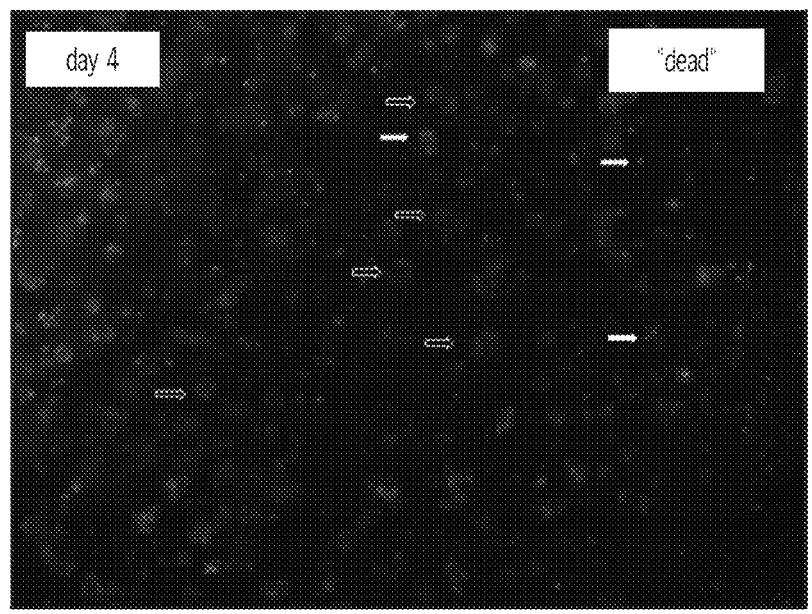

Results: Results for both the 3-cavity and 6-cavity cultures were similar. Following the print, cells were evenly distributed throughout the cell compartment up to the wall of each cavity (FIGS. 1C and 1D). Cell morphologies and densities persisted throughout the first four days (FIGS. 2A, 2C and 2D). As determined by a live/dead fluorescence assay, approximately 70% of the cells within the cultures maintained viability during the $1^{st}$ week (FIG. 2B). These numbers were calculated from the "dead stain" images as the autofluorescence of the collagen gel was too high to confidently assess the "live-positive" cells (FIGS. 2C and 2D). At 7 days of culture, both the 3-cavity and the 6-cavity cultures were fixed with 1.5% paraformaldehyde for histology assessment later by the investigative team.

For the second round of cultures, a) the 6-cavity assay with combined Heps/NPCs in the cell compartment was repeated, and b) the cavities were filled with Heps in collagen and by placing NPCs in the cell compartment. Both cultures were assessed for 14 days with one column of wells being live/dead assessed at week 1. During the last two days of culture (i.e. starting at day 13), the cultures were serum starved and then exposed to acetaminophen for 1 day followed by half of the wells being PFA fixed and the other half solubilized with urea for assessment.

Example 2

Static drug toxicity assay: provide 3D printed cultures of high density hepatocytes (+non-parenchymal cells) modeling viable liver tissue. The set differed from set 1 in which 3D cultures utilized low density hepatocytes in collagen.
Cells: Hepatocytes with their respective media and chemical compounds were provided by Nucro-Technics and shipped to ASLS's lab in Louisville, Ky.
Cell Printing: The assay replicated the 3D cell culture design used in the Example 1. The designs are based on "honeycomb" like structures within each well of a 96-well plate using a sacrificial material approach to create 6 cavities in the tissue mimic within each well (FIGS. 1A and 1B). For the experiment, primary Heps were mixed with primary NPCs, separated into three tubes and pelleted. Neutral, un-gelled collagen (0.3 ml of 3 mg/ml) was added to each pellet which was suspended and deposited around the printed sacrificial pillars. The pillars were then dissolved and washed away leaving cavities for media exchange. The 6-pillar design provides better media exchange with cell compartments by increasing surface area. The three separate Heps/NPC combinations represented 20 million Heps/ml, 15 million Heps/ml, or 10 million Heps/ml with each containing 1 million NPCs/ml.

Figure 4A:
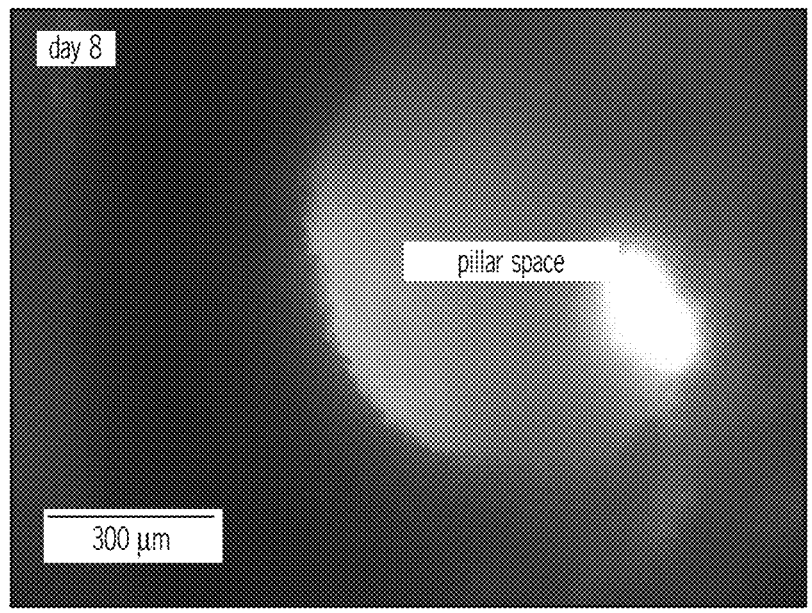
FIGS. 4A and 4B: Set forth phase images of the wall of a pillar cavity showing packed cells and structure.
Figure 4B:
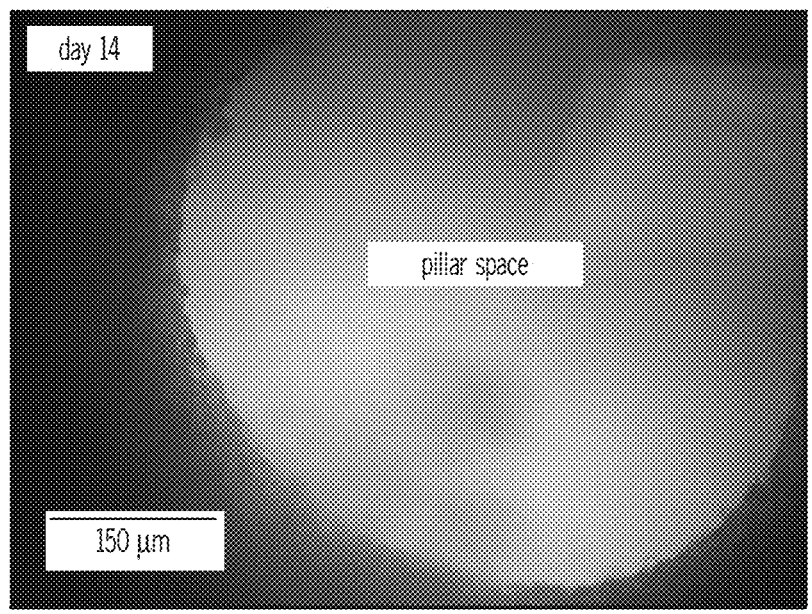
Figure 5:
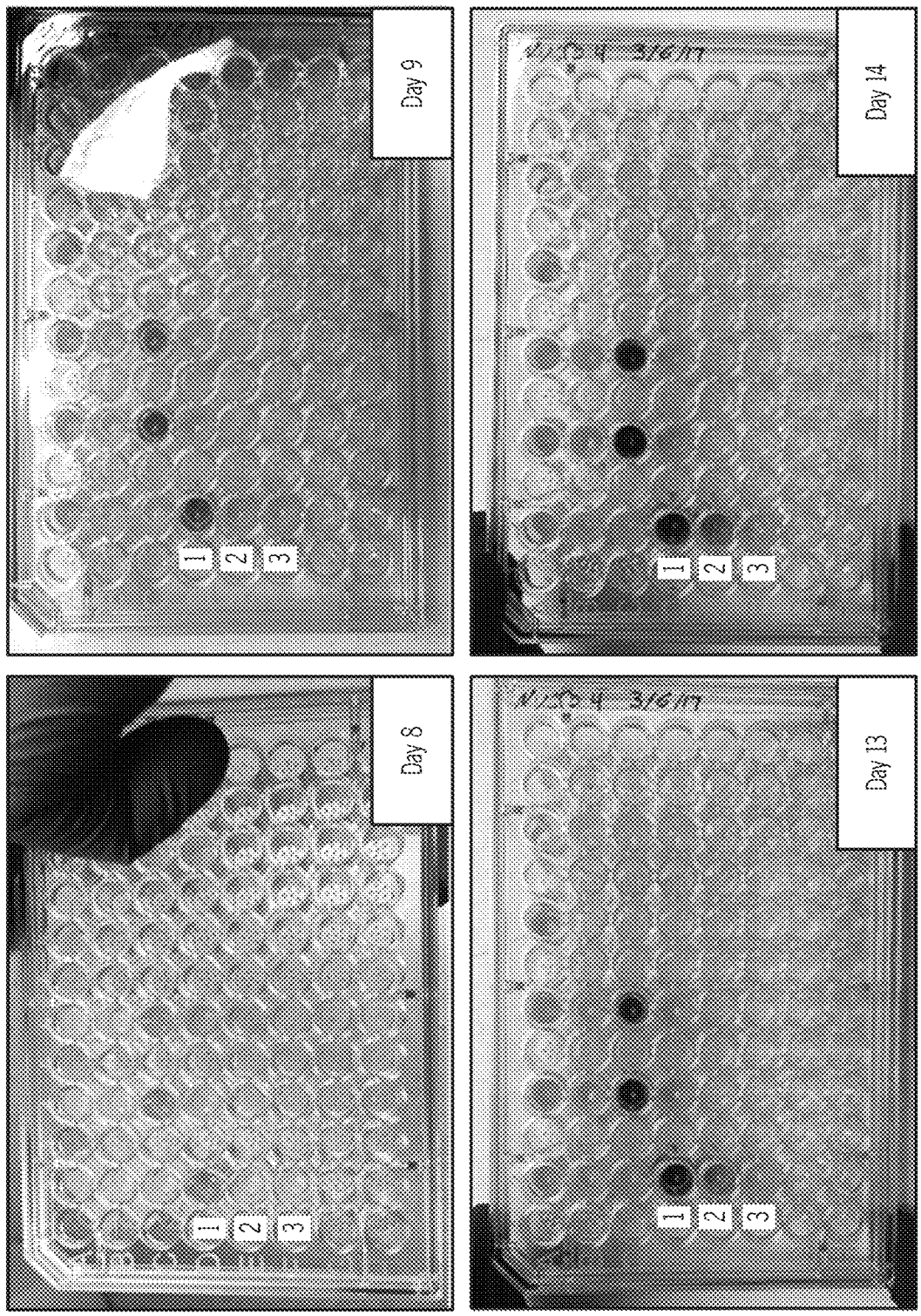
FIG. 5: Shows indicator changes in 3D Hepatocyte cultures treated with (1) high, (2) moderate, and (3) low dose acetaminophen. Refer to FIG. 2 for well configuration/composition.
Figure 6A:
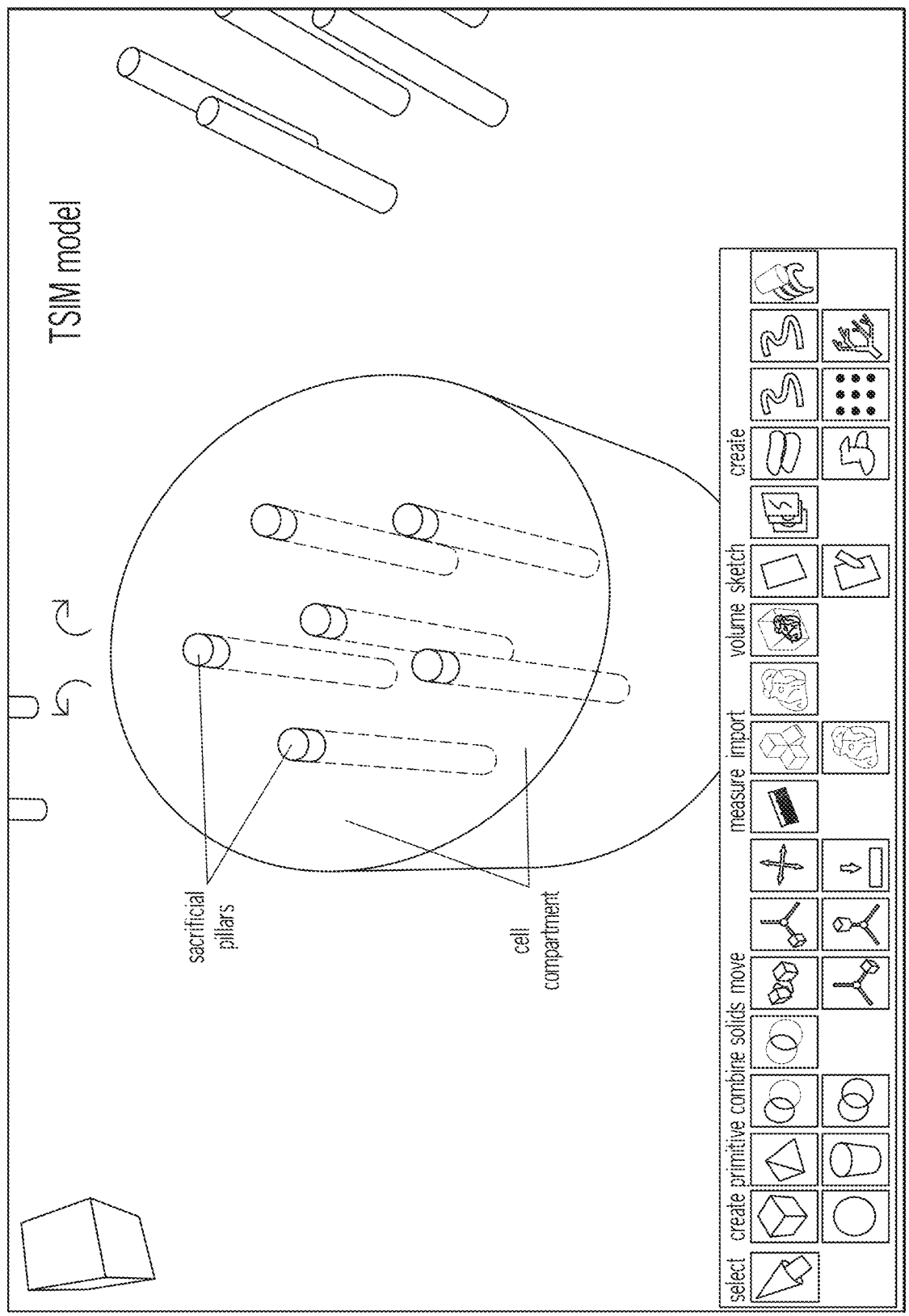
FIGS. 6A-6D: Exemplary embodiment in which five sacrificial pillars, 0.5 mm in diameter, are fabricated prior to the incorporation of a cells+microvessels (without collagen; so called "scaffold free") mixture around the pillars. Pillars are then sacrificed, leaving behind spaces within the tissue construct, around which the cells of the construct continue to grow and function.
Figure 6B:
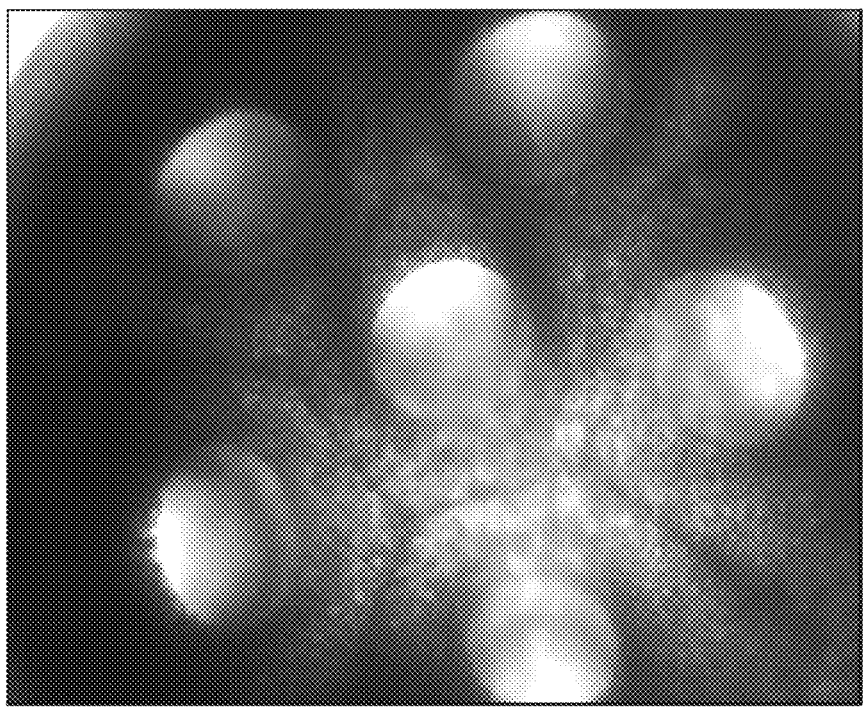
Figure 6C:
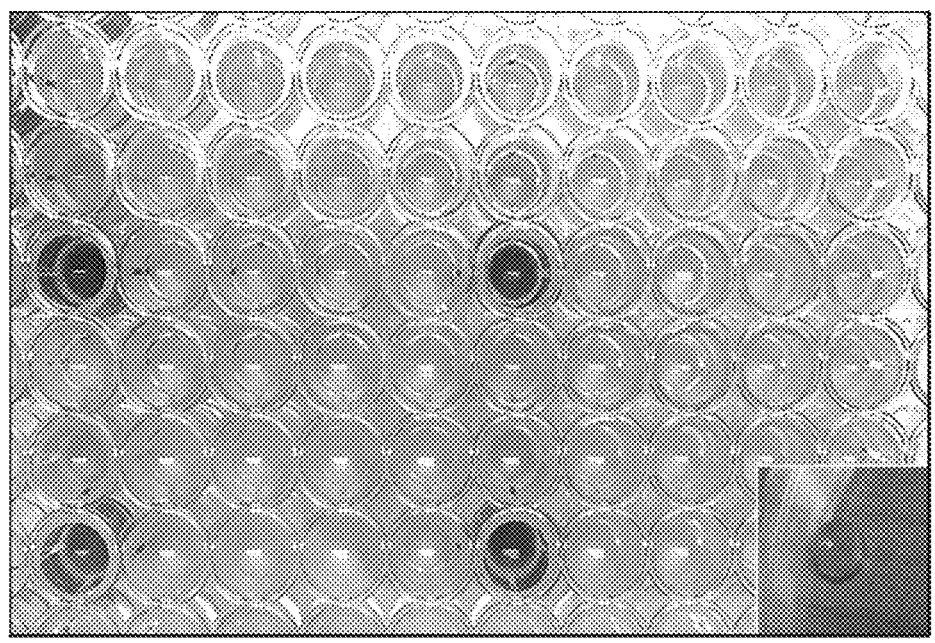
Figure 6D:
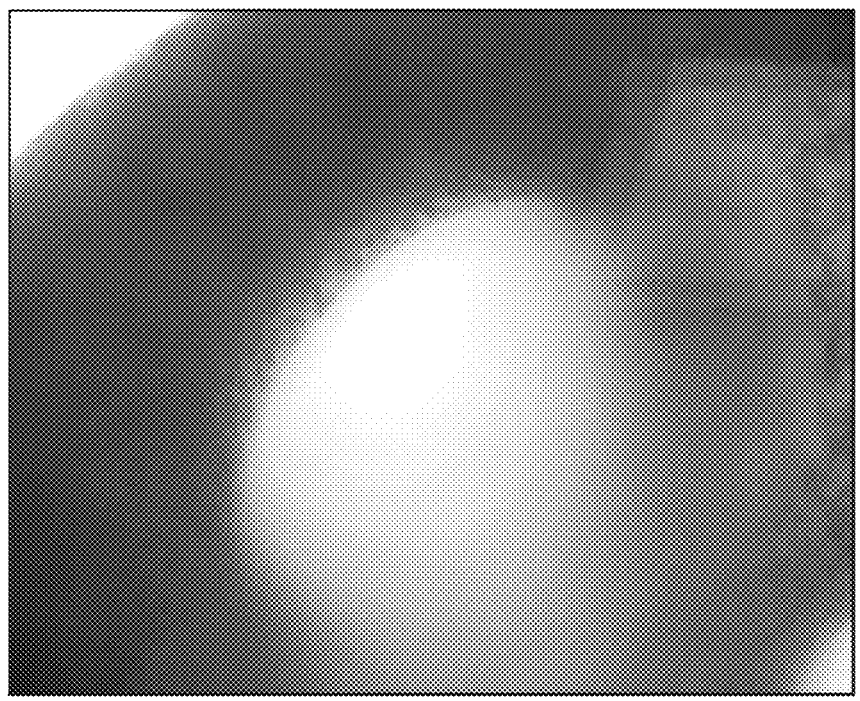
Figure 7A:
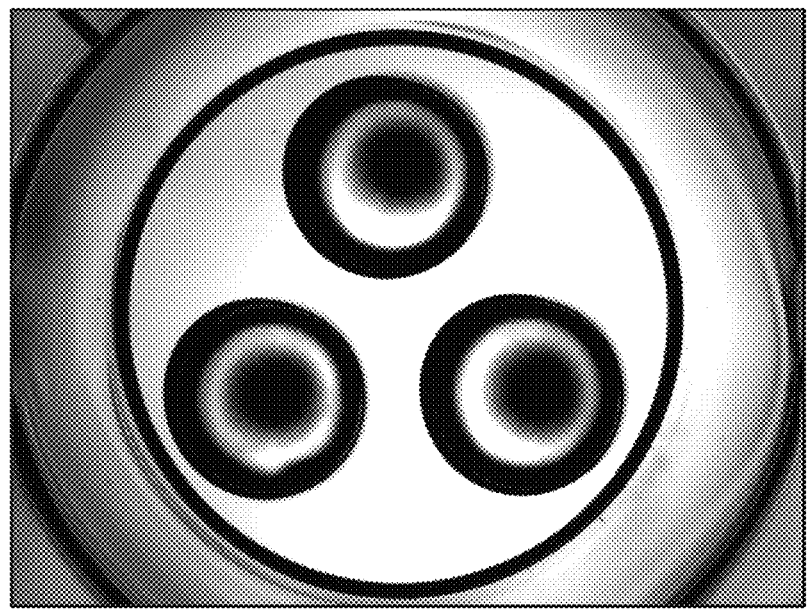
FIGS. 7A-7B: Exemplary embodiment of the invention in which 3 sacrificial pillars, 1 mm in diameter, are fabricated prior to the incorporation of a [cells+collagen] mixture around the pillars, highlighting the design flexibility. Pillars are then sacrificed, leaving behind empty pillar volumes/pillar spaces within the tissue construct, around which the cells of the construct continue to grow and function.
Figure 7B:
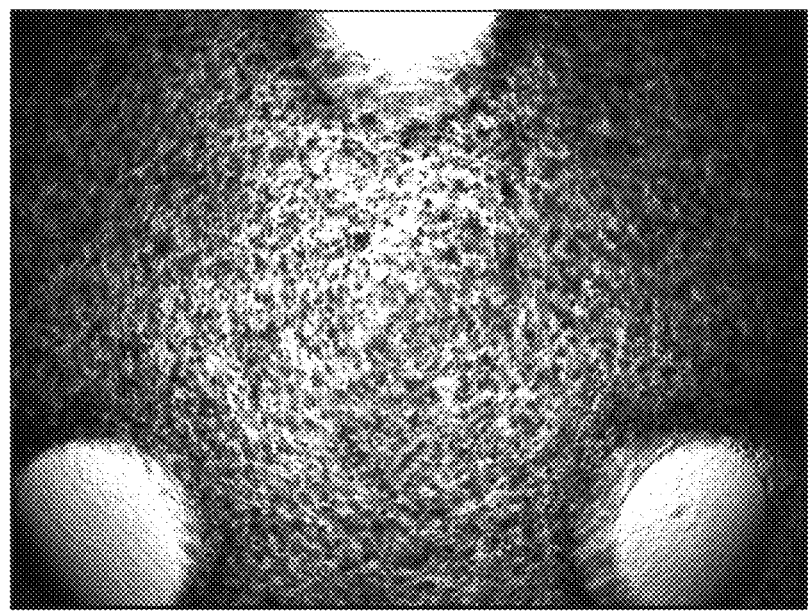
Figure 8A:
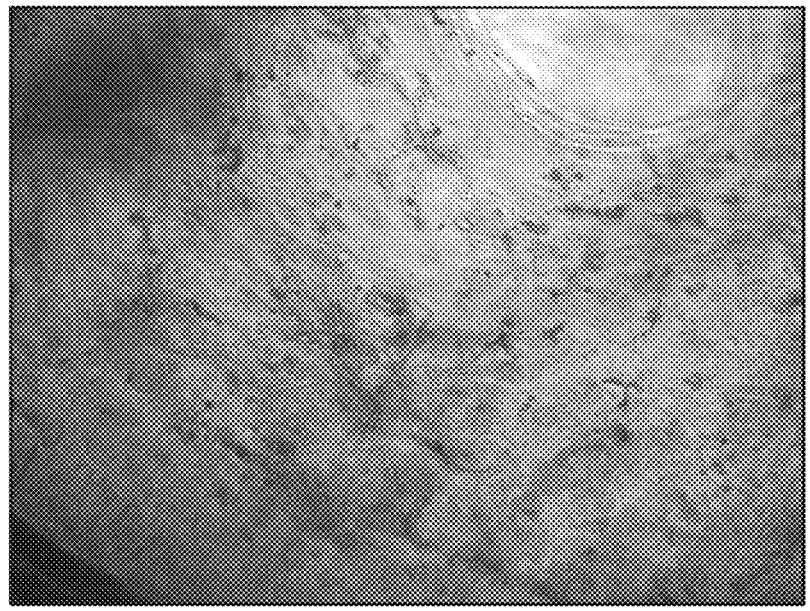
FIGS. 8A-8B set forth an illustrative embodiment in which sacrificial pillars are fabricated prior to the incorporation of a collagen containing intact microvessels cast around the pillars.
Figure 8B:
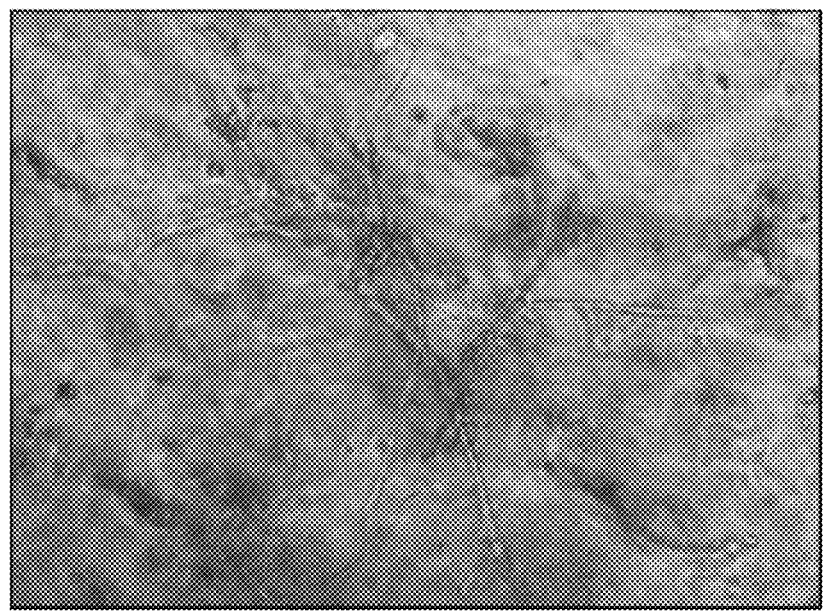
Figure 9A:
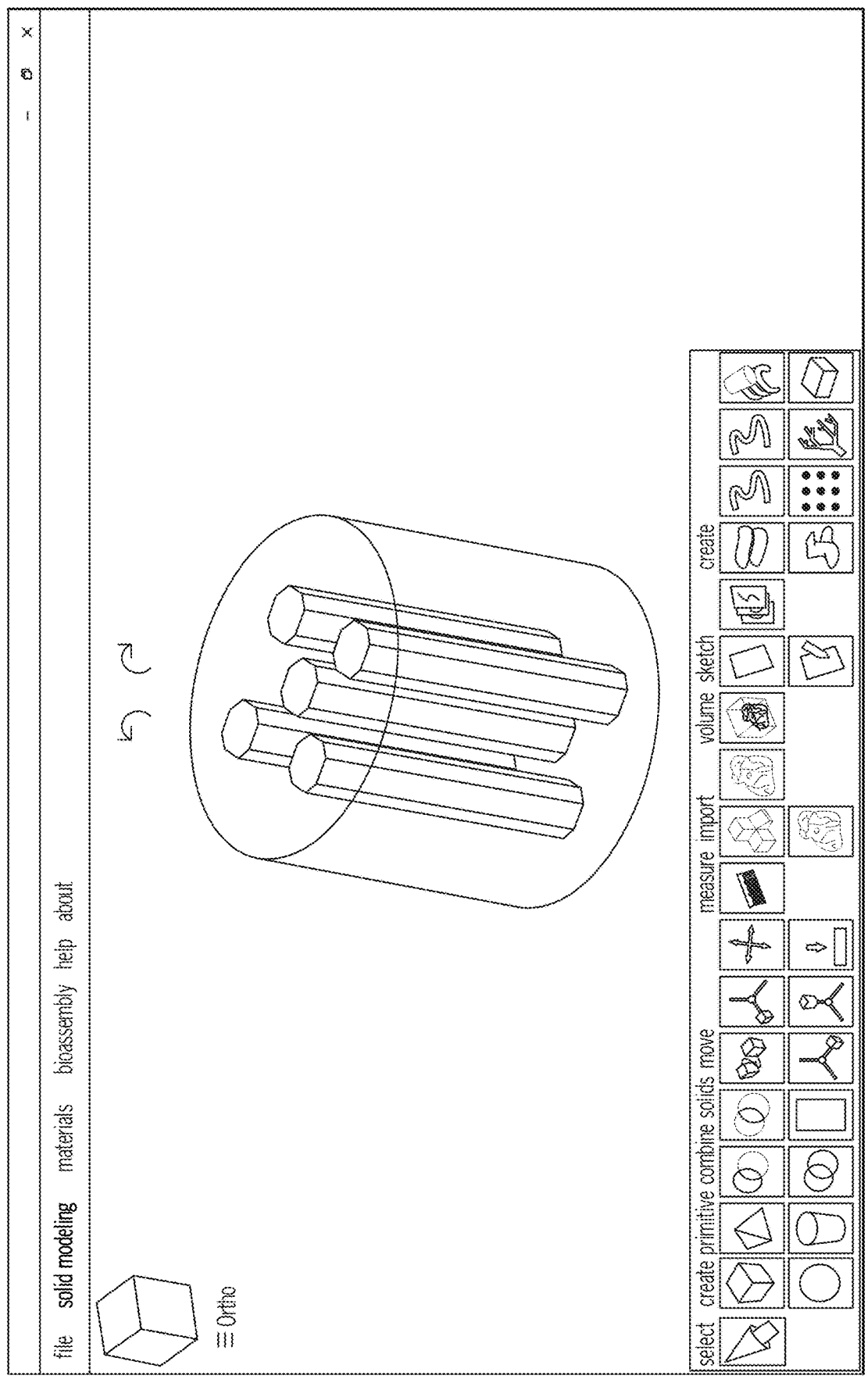
FIG. 9A: shows a TSIM-generated model of a tissue construct in which the sacrificial pillars (darker) are hexagonal in cross-section around which cells or cells+matrix are deposited (lighter)
Figure 9B:
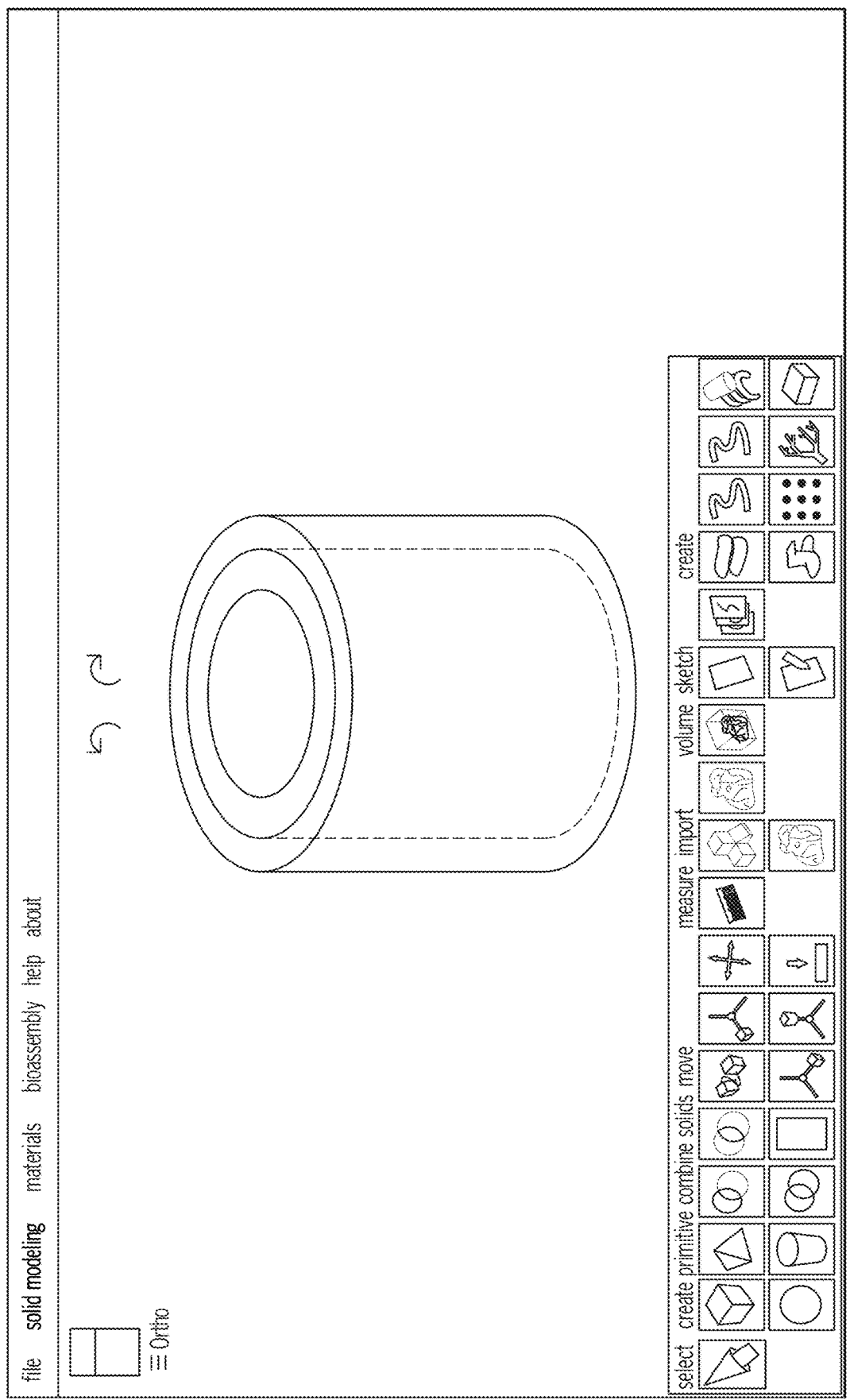
FIG. 9B: shows a TSIM-generated model of tissue construct in which the sacrificial pillar is a cylinder (darker) around and within which are deposited cells or cells+matrix (lighter).

Cultures were maintained on hepatocyte maintenance media (Lonza) for 7 days and then treated with select drugs for an additional 7 days (see FIG. 3).
As before, phase images were taken over the course of the 14-day study. Culture supernatants were collected and pooled starting with the first day of drug treatment (day 8) and continuing to the final day of treatment (day 14). All 3-D cultures were fixed with paraformaldehyde.
Results: Following the print and cell "casting", cells were densely packed up to the wall of each cavity (FIG. 4A). Cell morphologies and densities were difficult to assess, due to the high density of cells. However, cavity walls were maintained throughout the 14 day culture period, with clear evidence of individual cells at the cavity wall, including the apparent presence of matrix between cells (FIG. 4B). Wells receiving acetaminophen developed a brown color over the 7 days of treatment, the intensity of which reflected the dose of acetaminophen used (FIG. 5).

For the third set of static 3D cultures, the set 2 design is repeated with the inclusion of 80K isolated rat microvessel fragments/ml using the same high-density hepatocyte concentration throughout all cultures. This value is determined from the results of Set 2 showing the lowest of the 3 densities examined that still produced histologically competent liver mimics. Both cultures are assessed as before for 14 days with drug treatment starting at day 8.

Example 3

The following example sets forth a detailed protocol for modeling and printing an illustrative 6-pillar column array according to a specific embodiment of the invention into a flat-bottom 96 well plate, and for making and maintaining hepatocyte constructs. Other array configurations may require different or additional steps for modeling, preparing, printing or culturing and the adaptations will be readily apparent to one of ordinary skill in the part.

Modeling 6-Pillar Print in TSIM

Each pillar is an individual tube created from a sketch and positioned in the location desired. To create a tube;
Select Create a Sketch tool
Select the X-Z or Y-Z plane and click Create
Select the Create a Line tool (3 points connected in an angle). Right click to finish a line
Create a line that is 3 mm in height
Create 5 more lines, or copy and paste finished tube later
Select the Create a Tube from a Sketched Curve tool
Select sketched line
Enter radius (0.2 mm) and create (this tube can be copied and pasted using Ctrl-C and Ctrl-V. Pasted objects will appear in object list but will initially be occupying the same position as the original object. Move the object to visualize it)
Move tubes to desired position. Center tube will have a position of (−106.3921, −53.9638, 1.5000) in the most forward left well. This will be the starting position from which a pattern will be generated
Arrange 5 tubes around center tube. For exact locations, use following algorithm where $P_i$=position of exterior tube number i (1, 2, 3, 4, 5), $X_c$=X coordinate of center tube, $Y_c$=Y coordinate of center tube, r=radius of well=1.5525 mm, and n=number of exterior pillars=5, $P_iX$=X coordinate of tube i, $P_iY$=Y coordinate of tube i.
$P_i=(P_iX, P_iY)$
$P_iX=X_c+r*\cos(i*360/n)$
$P_iY=Y_c+r*\sin(i*360/n)$
Sample: Position of exterior tube 3, $P_3=(P_3X, P_3Y)$
 $P_3X=-106.3921+1.5525*\cos(3*360/5)$
  $P_3X=-107.6481$
 $P_3Y=-53.9638+1.5525*\sin(3*360/5)$
  $P_3Y=-54.8763$
   $P_i=(-107.6481, -54.8763)$
These values are typed into the "center" coordinate space for each tube in the Transform section of the right side property panel
Note that all Z coordinates should be the same (1.5 for 3 mm tall tubes)
After each tube is in place, select all six tubes and assign the desired material from the materials list. A new material can be made, or current material can be edited if needed in the materials tab.
With all tubes selected, click the Generate a Pattern from a Selected Solid tool and enter the following information for a 96 well plate
Horizontal Count: 12
Horizontal Spacing: 8.899 mm
Vertical Count: 8
Vertical Spacing: 8.964 mm
Yaw: −0.500 deg Create the pattern. All tubes should have the desired material already selected for them The 96 well plate template can be used to verify the location of the tubes. Ensure that the well plate has the lock icon closed in the property panel. This will ensure that the plate template cannot accidentally be moved.

Make sure the box for Precise Tip Detect on the right side Property Panel is checked. This will instruct the BioAssemblyBot to perform a tip detect in both X and Y axes. This will help ensure that any bend in the needle is accounted for When the objects are placed in a satisfactory location, click on the Bioassembly tab and then Send Print Job. This will send your current file to the BioAssemblyBot Pluronic Sterilization For tissue culture, it is advised that all materials that came into contact with the pluronic be sterilized. This includes the needle, barrel, piston and the pluronic itself. All items can be steam sterilized on a pre-vacuum cycle. The pluronic should only take up about 30% of the total volume of its container, as the pluronic will boil and expand. After the cycle is complete, place the jar at 4° C. overnight. After all of the pluronic has been suspended, it is ready to be used. Some instances require the pluronic to sit for several days at 4° C. before being completely suspended. A stir table may assist in reducing time for suspension.

Preparing to Print

Several steps prior to printing need to be taken in order to allow for an optimal print.
These steps are as follows
In a biosafety cabinet, load the print material into a clean barrel with a blue cap on the tip. Pluronic F-127 can be added cold, as this will make it liquid and easy to pour
De-gas the material while it is still liquid. This will require that the materials stay cold (<14° C.). Degassing can be done through sonication or vacuum aspiration.
Add the white piston into the barrel and push down with some twisting as needed until there is a minimal amount of air between the piston and pluronic.
Allow the pluronic to reach room temperature to gel completely
Load the barrel into the ambient tool by attaching and fully tightening the blue air adapter to the top of the barrel and pressing the barrel into the metal clip
Be sure that the airline is not twisted or kinked in the underside of the tool head
Pull the barrel as far down in the metal clip as possible, so that the bottom of the air adapter is nearly resting on the top of the metal clip. This will help prevent kinks in the air line and allow the tip detect to see the needle more readily
Remove the blue tip cap and place a 0.5 in long 22 gauge needle (blue) on the barrel tip
Other needle diameters can be used, but the previous plates have been printed with the 22 gauge. If other tips are used, alterations in the print parameters will need to be made to adjust for resistance variations
0.5 inch needles are required as shorter needles will not reach the bottom of the well without impacting the needle hub Place the tool and barrel into bay 1
Prime the needled so that as the print begins, there is material at the end of the needle ready to extrude. To do this;
Command the BioAssemblyBot to pick up the tool from bay 1
Open the Control tab
Select the Other tab
Select Retrieve tool
Select Bay 1 from drop down menu
Confirm Retrieve tool
After the Bot picks up the tool and returns to the home position, type in the desired priming pressure. For the 0.5 inch 22 gauge needle, start at 20 PSI
Press the Red button next to the word "On". This will begin the flow of air
There is a time limit to how long this dispense will last. If the button is green, air is being dispensed, if it is red, air is not being dispensed. Simply press the button again if it stops before you have finished priming
Use the "+" and "−" buttons to increase or decrease the pressure. This will also reset the internal timer. You can also type in a new pressure while a prime is occurring, which also resets the timer.
For the 20 gauge needle, 20 PSI will likely be too low. Increase the pressure by 1 PSI until a steady stream of pluronic is being extruded
Continue priming until there are no apparent air bubbles remaining in the stream. These air bubbles will appear as either a spitting of pluronic out of the needle, or breaks in the stream. Priming will usually take 1-2 full cycles of the timer (i.e. once a steady stream rate has been established, allow the dispensing timer to run out twice. Each cycle takes about 10-15 seconds.
Wipe the end of the needle with a clean towel to remove any excess pluronic
Perform a tip to stage offset. Because the bottom of the tubes in TSIM have a Z value of 0, the tip to stage offset will need to be set inside of the 96 well plate. To do this
Place the 96 well plate onto the print stage so that the plate is up against the positive stops. The plate should be placed so that the row of 12 wells in running left to right and the column of 8 wells is forward to back
Use the move commands on the HMI to move the Bot with tool to the forward left well (any well will work, but this is the easiest one to see).
Select the Control tab
Select the Move tab
Use the dial to set the distance for the Bot to move with each command
X and Y movements are on the left side of the screen while Z movements are on the right side
TIP: it is always easier to use large movements to move the Bot to a rough location, then smaller movements to move the Bot to the exact location. Always be mindful of the distance that is set for the Bot before moving. The stage is on springs and will give if the Bot hits it, but it is likely to bend a needle or crack a well plate
Slowly move the Bot down so that the needle is in the center of the well and just touching the bottom of the well
The precision of this calibration step is important to ensuring the correct outcome of the print TIP: it is easier to visualize the tip relative to the bottom of the well if you are at eye level with them. Shadows and reflections from the needle are very useful in this process TIP: it is wise to use very small movements when the needle is close to the stage (0.1 mm-0.01 mm). This makes visualization more difficult but ensures the accuracy of the process.

TIP: if you are unsure of the location of the bottom of the well relative to the needle or if you think the needle may be contacting the well, set the movement distance to 0.5 mm or greater and move the Bot up in Z. If the stage rebounds up, if the plate moves or if the needle flexes, then the needle was on the bottom of the well. Move up again until you don't see any signs of the needle touching the plate, then move down in a smaller increment. If there were no signs of the needle touching the plate, move back down by the same set distance and continue moving in the small increments.

Once the needle is just touching the bottom of the well, but not causing it to bend, move the Bot up by 0.2 mm. It will be difficult to visualize this, so watch the HMI. Once the command has been issued, the buttons will become gray for a moment while the Bot completes the command. If the buttons gray out momentarily, then it is safe to assume that the Bot moved.

Open the Calibration tab

Select the Tip to Stage Offset tab

Press the Perform Tip to Stage Offset button. The Bot will move to the tip sensor in the back left corner After the tip to stage offset has been measured, command the Bot to return the tool to Bay 1 through the Control tab and Other tab Printing with BioAssemblyBot Once the model has been created in TSIM and sent to the BioAssemblyBot, all remaining actions will take place from the BioAssemblyBot HMI. The only time that TSIM modelling will need to be revisited is if alterations in the structure or printing parameters need to be made. To print;

Make sure the BioAssemblyBot has been prepped, that is tip to stage offset has been determined, print needle has been primed and the well plate is in position with the lid off Under the Print tab, select the desired print from the list Confirm that the structure in the preview window has all desired structures (tubes) and no additional structure (well plate)

Press Start

Make sure print materials are in the correct bay. This screen will tell you what bay the BioAssemblyBot is expecting the materials to be in. If they are not in the correct bay, open the door and move them by hand Press Confirm The HMI will automatically take you to the Status tab with a progress bar and will remain on this tab until the print is finished As the BioAssemblyBot is in motion, continue to watch. If there are any undesired movements that could cause a collision, press the E-stop button (red button on a yellow base on the upper left side of the frame). This will cause all functions of the BioAssemblyBot to stop immediately, called a "hard stop". This will also stop the print if there is one in progress, therefore you will have to restart the print. In order to release the depressed E-stop, turn the button clockwise until it physically pops back to its original position. This will not cause the BioAssemblyBot to continue what it was originally commanded. The original command has been terminated and the Bot is awaiting a new command.

The HMI status window during a print will have a pause button that will temporarily stop the print, but can then be resumed and the Bot will start where it left off. A pause command is not a "hard stop" and the BioAssemblyBot will continue with a line and then pause at the end of the line.

Troubleshooting

Print parameters on the BioAssemblyBot will need to be adjusted over time or experimentally. For the 6-pillar print, there are several things that can cause for a misprint, from the print parameter settings or an inaccuracy during the preparation. The following is a list of potential issues and how to resolve them.

Tip detect failure on multiple attempts

The tip detection laser failed to determine the location of the needle. Try to slide the barrel up and back down while still in the clip, then make sure that the barrel is as low in the tool as possible The needle may be bent. Either straighten the needle or replace with a new needle No material is being extruded from the needle Perform a needle priming procedure (in Preparing to Print section) and increase the pressure until material begins to flow. If the pressure is more than 20 PSI above the expected extrusion pressure, the needle is likely clogged. Pluronic will begin to dry in the needle if left out for more than 2 hours without extrusion. Replace the needle Too much material is being extruded from the needle during a print This is likely because the pressure is too high, however a slow print speed can contribute to this. First, adjust pressure, then speed if the pressure is near the minimum for extruding the material The tube has a wide base but becomes thinner toward the top The start delay parameter is likely too high. This parameter is used to begin dispensing before the Bot starts to move in the print to help establish a base of material. If this is too high, it will cause too much material to be dispensed at the beginning. Decrease the start delay The tube prints well at the beginning, but breaks half way up This is usually because the pressure is too low or the print speed is too high. Increase the pressure slightly so that more material will be extruded and prevent the break. Adjusting print speed can have too great of an effect and cause the pillar to become quite thick The needle has pluronic curling up on the end and is not printing in the well This can be from two causes. The tip to stage offset could have been calibrated improperly, resulting in the print to begin above the well plate, not on it. Recalibrate the tip to stage offset as described in the Preparing to Print section. If the issue persists, increase the start delay to allow the Bot more time to form the initial material base The BioAssemblyBot is not printing in the center of the wells
  Ensure that the well plate is contacting the positive stops on the stage completely. Any movement can cause a magnified effect on the wells toward the edge. If the well plate is in the proper position, make sure the tube pattern was created in TSIM using the parameters listed in the Modeling 6-Pillar Print in TSIM section. If that was also done correctly, the tubes may need to be moved slightly. In TSIM, select all objects and move them the desire direction and distance. If the print seems tilted, delete all of the tubes except for the ones in the forward left well. Regenerate the pattern as described in the Modeling 6-Pillar Print in TSIM section, but adjust the yaw accordingly
The controls on the HMI are grayed out
  Either the E-stop has been depressed and not released or one of the doors is ajar. Make sure the E-stop button is released by twisting it clockwise and that all doors are closed all the way Hepatocyte Construct Protocol After successfully printing the 6-pillar structure in the desired wells, the remainder of the process can take place in a biosafety cabinet to maintain sterility. After the print is complete and it is safe to open the doors to the BioAssemblyBot, replace the well plate lid and transfer it to the biosafety cabinet if you plan to immediately begin making the cell constructs. If not, the well plate can be stored in an incubator with 100 percent humidity. This will prevent the pluronic from drying out. The steps for making the hepatocyte constructs is as follows:
  Collagen: Collagen is used as the extracellular matrix in these constructs. The materials needed to make collagen are:
    High concentration rat tail collagen type 1 (Corning ref #354249)
    4× DMEM
      1 g DMEM low glucose powder (Gibco ref #31600-026)
      0.37 g NaHCO$_3$
      0.476 g HEPES
      Dissolved in total volume of 25 mL sterile water
      Filter sterilized
    Sterile water
  The final concentration of collagen will be 3 mg/mL with 1× DMEM. Therefore 5 mL of collagen from a 10 mg/mL high concentration stock calls for 1.5 mL high concentrated collagen, 1.25 mL 4× DMEM and 2.25 mL sterile water
    TIP: Prepare to make about 0.5 mL more collagen than intended to use. Some volume will be lost in the preparation steps
    TIP: When mixing the collagen, it is advised to use a cold pipet to prevent gelling
    TIP: While mixing, be gentle as to avoid air bubbles. These can be very difficult to remove
  Collagen will need to be kept sterile and on ice until ready to use. The collagen will begin to gel at warmer temperatures Cell Culture Determine concentration of hepatocytes and non-parenchymal cells for the constructs and total number of cells needed
Thaw hepatocytes briefly in 37° C. water bath and add to thawing media
Thaw NPCs briefly in 37° C. water bath and add to separate thawing media
Remove appropriate volume of media to attain desired total number of cells. Do this for both hepatocytes and NPCs
Add both desired volumes of hepatocyte and NPC solutions together and centrifuge at 60 XG for 10 minutes. The hepatocytes will help pull the NPCs into the pellet
Aspirate supernatant
Re-suspend cell pellet in desired volume of collagen
Using pipet, dispense 90 uL of collagen cell suspension into each well. This will allow a small amount of the pluronic pillar to remain uncovered
  TIP: place tip of pipet against well wall and dispense slowly, as to not disturb pluronic pillars
  TIP: If using a 1 mL serological pipet, do not attempt to dispense past 0.3 mL residual volume. This could cause a quicker than expected dispense and overflow of the well
Once all wells are filled, place plate in incubator for 30 minutes to allow collagen to gel
After gelation, add 100 uL of hepatocyte maintenance media to each well. This will begin nourishing the cells as well as dissolving the pluronic gel
Place back in incubator for 30 minutes
Remove media and dissolved pluronic from the well via micropipette set to 150 uL carefully
  TIP: Leave the well plate flat and place micropipette tip at an angle in the well. This will prevent the cell construct from pulling away from the well and into the micropipette tip
Add 100 uL of fresh media to each well and return to incubator
Change media in this way every day
Drug treatments are administered is this way as well

What is claimed:
1. A column array comprising:
a set of columnar spaces, each columnar space comprising:
  a base;
  one or more pillar spaces substantially devoid of material, wherein:
    the one or more pillar spaces are defined by removal of one or more sacrificial pillars comprising a sacrificial material; and
    the one or more pillar spaces extend from the base within the columnar space; and
  a cellular volume,
wherein the one or more pillar spaces are surrounded by cellular volume, said cellular volume comprising viable cells.

2. The column array according to claim 1, wherein the one or more pillar spaces extend substantially vertically from the base.

3. The column array according to claim 1, wherein the cellular volume comprises a hydrogel matrix comprising the viable cells.

4. The column array according to claim 1, wherein the cellular volume comprises the viable cells without a hydrogel matrix.

5. The column array according to claim 1, wherein the viable cells are selected from one or more of normal cells, diseased cells, stem cells, endothelial cells, stromal cells, myocardial cells, hepatocytes, renal cells, tumor cells, liver cells, pancreatic cells, muscle cells, brain cells, kidney cells, and patient-specific cells.

6. The column array according to claim 3, wherein the hydrogel matrix is selected from a natural hydrogel, a synthetic hydrogel, and hybrid natural and synthetic hydrogels.

7. The column array according to claim 6, wherein the natural hydrogel is selected from one or more of a collagen, gelatin, fibrin, and a polysaccharide selected from hyaluronic acid (HA), agarose, alginate, and chitosan, and the synthetic hydrogel is selected from one or more of polydimethylsiloxane (PDMS), polyethylene glycol (PEG), poly(lactic-co-glycolic acid) (PLGA) and polyglycerol sebacate (PGS) polymers.

8. The column array according to claim 1, wherein the cellular volume further comprises a microvasculature.

9. The column array according to claim 8, wherein the microvasculature is formed from adding substantially intact native microvessels to the cellular volume and subjecting the microvessels to maturing conditions.

10. The column array according to claim 9, wherein the intact native microvessels derive from adipose tissue.

11. The column array according to claim 1, wherein the pillar space comprises at least one inlet port.

12. The column array according to claim 1, wherein at least two pillar spaces are in fluid communication via at least one cross-connecting channel.

13. The column array according to claim 1, wherein the column array is static or perfusable.

14. The column array according to claim 1, wherein the one or more pillar spaces comprises a plurality of pillar spaces, said plurality of pillar spaces comprising:

an axial pillar space, located at an axial position on the base; and one or more outside pillar spaces, located between the axial position and an edge of the base, wherein the one or more of outside pillar spaces are in fluid communication with the axial pillar space.

15. The column array according to claim 11, further comprising an external perfusion system connected to the pillar space.

16. A multiple well-plate platform comprising a column array according to claim 1 in each of a plurality of wells.

17. The multiple well-plate platform according to claim 16 comprising 384, 96, 49, 24, 12, or 6 wells.

18. A method of screening putative agents for specific cellular toxicity, the method comprising providing a mutiwell plate according to claim 16, adding a composition of a putative agent into a pillar space of a set of wells in the plate, and measuring changes in viability of cells in the cellular volume versus a control.

19. A method of screening putative agents for effect on angiogenesis, the method comprising providing a multiwell plate according to claim 16, wherein the cellular volume comprises a microvasculature derived from adding substantially intact native microvessels to the cellular volume and subjecting the microvessels to maturing conditions; adding a composition of a putative agent into the pillar space, and measuring changes in the microvasculature versus a control.

20. The method according to claim 18, wherein the pillar space is connected to a perfusion system and the composition of a putative agent perfuses the cellular volume.

* * * * *